United States Patent
Kim et al.

(10) Patent No.: US 7,794,799 B1
(45) Date of Patent: Sep. 14, 2010

(54) PROCESS FOR PRODUCING ARRAY PLATE FOR BIOMOLECULES HAVING HYDROPHILIC AND HYDROPHOBIC REGIONS

(75) Inventors: Woon-bae Kim, Suwon (KR); Chang-ho Cho, Suwon (KR); Kae-dong Back, Seoul (KR); Hwan-young Choi, Anyang (KR)

(73) Assignee: Samsung Electronics Co., Ltd., Suwon, Kyungki-do (KR)

( * ) Notice: Subject to any disclaimer, the term of this patent is extended or adjusted under 35 U.S.C. 154(b) by 944 days.

(21) Appl. No.: 10/438,334

(22) Filed: May 15, 2003

(30) Foreign Application Priority Data

May 15, 2002 (KR) .............................. 2002-26730

(51) Int. Cl.
*B05D 3/00* (2006.01)

(52) U.S. Cl. ................. 427/532; 435/287.1; 435/287.8; 427/2.11; 427/457; 427/490; 427/450; 427/461; 436/518

(58) Field of Classification Search ..................... 427/2, 427/414; 436/45, 94, 165; 422/57, 62–64; 435/7.1; 137/15.01
See application file for complete search history.

(56) References Cited

U.S. PATENT DOCUMENTS

| | | | | |
|---|---|---|---|---|
| 4,202,805 A | * | 5/1980 | Kato et al. | ................... 525/384 |
| 5,063,081 A | * | 11/1991 | Cozzette et al. | ................ 435/4 |
| 5,079,600 A | | 1/1992 | Schnur et al. | |
| 5,688,642 A | | 11/1997 | Chrisey et al. | |
| 5,958,345 A | | 9/1999 | Turner et al. | |
| 6,008,892 A | | 12/1999 | Kain et al. | |
| 6,121,048 A | * | 9/2000 | Zaffaroni et al. | ............... 436/45 |
| 6,210,894 B1 | | 4/2001 | Brennan | ........................ 435/6 |
| 6,548,020 B2 | * | 4/2003 | Okamoto et al. | ........... 422/68.1 |
| 6,833,542 B2 | * | 12/2004 | Wang et al. | .................. 250/251 |
| 7,007,710 B2 | * | 3/2006 | Heller et al. | ............. 137/15.01 |
| 2001/0021534 A1 | * | 9/2001 | Wohlstadter et al. | ........ 436/518 |
| 2002/0150506 A1 | * | 10/2002 | Okamoto et al. | ........... 422/68.1 |
| 2003/0157317 A1 | * | 8/2003 | Ito et al. | ..................... 428/323 |

FOREIGN PATENT DOCUMENTS

| | | |
|---|---|---|
| CA | 2 260 807 | 1/1998 |
| DE | 196 28 928 A | 1/1998 |
| EP | 0 895 082 A | 2/1999 |
| EP | 1121947 A1 * | 8/2001 |

* cited by examiner

*Primary Examiner*—N. C. Yang
(74) *Attorney, Agent, or Firm*—Lee & Morse, P.C.

(57) ABSTRACT

A method for manufacturing an array plate for biomolecules includes coating a surface of a substrate with a hydrophobic material to form a hydrophobic layer having initial hydrophobic properties, etching the hydrophobic layer through an etch mask placed thereon to form a hydrophilic binding site, removing the etch mask, and processing the remaining region of the hydrophobic layer to recover the initial hydrophobic properties. A method for manufacturing a biochip using this array plate, includes processing the surface of the hydrophilic binding site of the array plate to increase an affinity of biomolecules to the hydrophilic binding site, and applying a solution containing biomolecules to the surface of the hydrophilic binding site.

40 Claims, 4 Drawing Sheets

FIG. 1

(Prior Art)

FIG. 2

(Prior Art)

PROCESS FOR PRODUCING ARRAY PLATE FOR BIOMOLECULES HAVING HYDROPHILIC AND HYDROPHOBIC REGIONS

BACKGROUND OF THE INVENTION

1. Field of the Invention

The present invention relates to a method for manufacturing an array plate of hydrophilic and hydrophobic regions based on semiconductor manufacturing processes and a method for manufacturing a biochip by immobilizing biomolecules on the array plate.

2. Description of the Related Art

According to a conventional method for manufacturing a nucleic acid array plate including hydrophilic and hydrophobic regions, microdroplets of reactant solution spread by means of a piezoelectric pump can be migrated onto separate binding sites on the array plate due to a difference in surface tension between the hydrophilic and hydrophobic regions.

Figure 1:
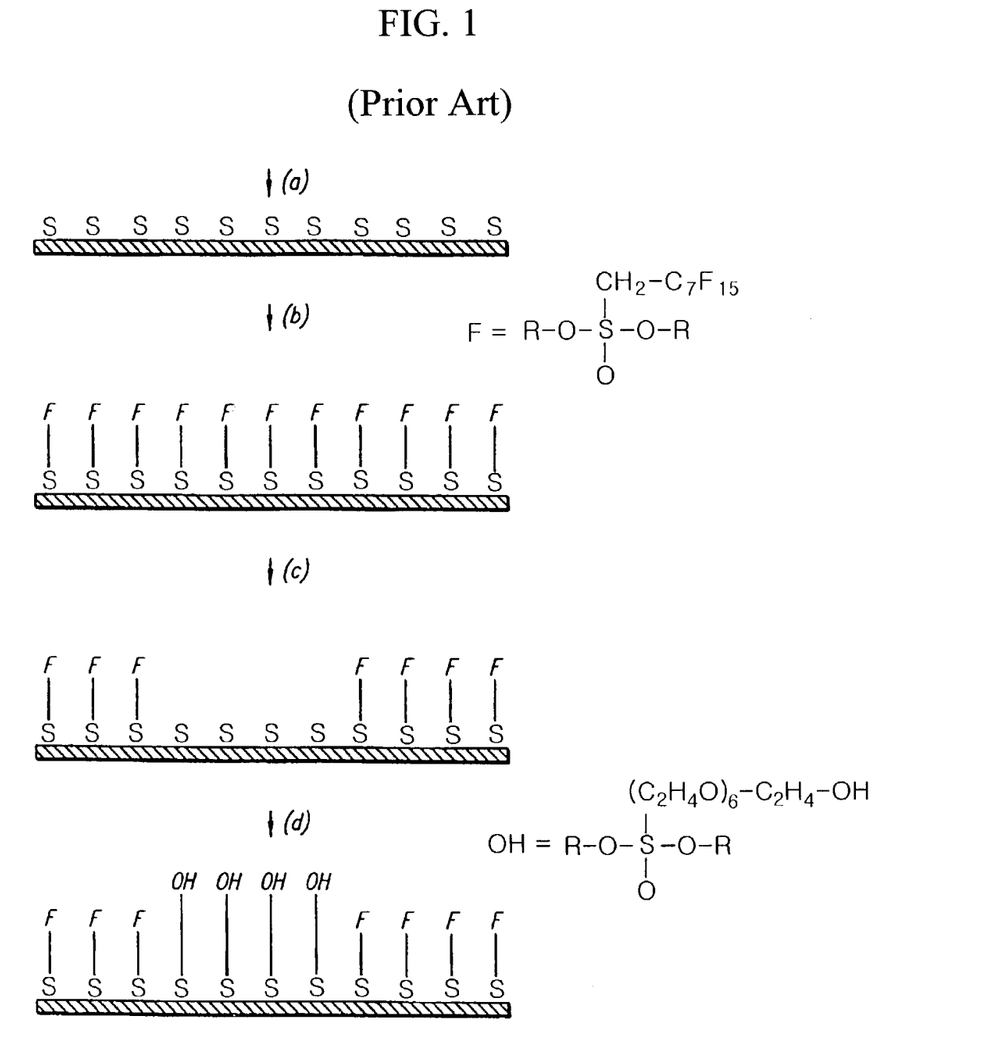
FIGS. 1 and 2 illustrate examples of conventional methods for manufacturing nucleotide array plates.

In particular, as illustrated in FIG. 1, the conventional method for manufacturing the nucleic acid array plate involves: (a) coating a support surface with a positive or negative photoresist which is subsequently exposed to light and developed to create a patterned region of a first exposed region; (b) reacting the first exposed region with a fluoroalkylsilane to form a stable fluoroalkylsiloxane hydrophobic matrix on the first exposed region; (c) removing the remaining photoresist to form a second exposed region; and (d) reacting the second exposed region with a hydroxy or aminoalkylsilane to form functionalized hydrophilic binding site regions.

Figure 2:
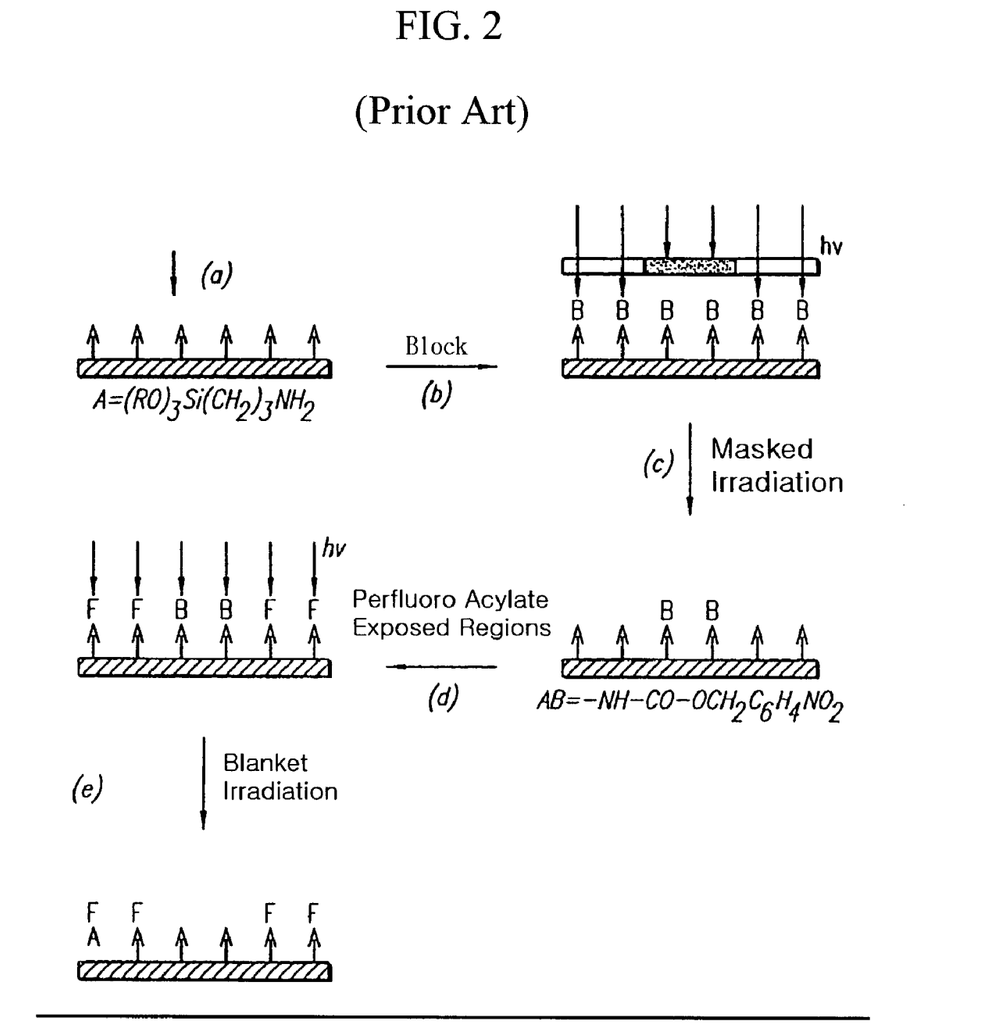

Alternatively, as illustrated in FIG. 2, the nucleic acid array plate may be manufactured by: (a) reacting a support surface with a hydroxy or aminoalkylsilane to form a functionalized hydrophilic support surface; (b) reacting the support surface from step (a) with o-nitrobenzyl carbonyl chloride acting as a temporary photolabile blocking agent to provide a photoblocked support surface; (c) exposing the photoblocked support surface of step (b) to light through a mask to create unblocked areas on the support surface with unblocked hydroxy or aminoalkylsilane; (d) reacting the exposed surface of step (c) with perfluoroalkanoyl halide or perfluoroalkylsulfonyl halide to form a stable hydrophobic (perfluoroacyl or perfluoroalkylsulfonamido)allyl siloxane matrix; and (e) exposing the remaining photoblocked support surface to create patterned regions of the unblocked hydroxy or aminoalkylsilane as functionalized hydrophilic binding site regions.

In practice, however, it is difficult to control the thickness of the molecular layer, which is measured in tens of angstroms, using these methods for manufacturing nucleic acid arrays. Moreover, the strength of the thin molecular layer made using these methods is weak. Additionally, since the molecular layer is thin and transparent, it is difficult to distinguish the hydrophilic and hydrophobic regions of the molecular layer from one another for sample applying through a nozzle. It is also difficult to automate pattern detection by a detector system. In addition, the molecular layer is formed of materials which are unusual in the manufacture of semiconductor devices, and it is difficult to establish an alignment key for the exposure of such a molecular layer according to general semiconductor manufacturing processes.

SUMMARY OF THE INVENTION

According to a feature of the present invention, there is provided a method for manufacturing an array plate for biomolecules that includes distinct hydrophilic and hydrophobic regions, based on conventional semiconductor manufacturing processes and in which the thickness of the thin material layers is easily controlled.

According to another feature of the present invention, there is provided a method for manufacturing a biochip using an array plate for biomolecules formed using the above method, with high accuracy and high yield.

According to an aspect of an embodiment of the present invention, there is provided a method for manufacturing an array plate for biomolecules, the method comprising: (a) coating a surface of a substrate with a hydrophobic material to form a hydrophobic layer; (b) etching the hydrophobic layer through an etch mask placed thereon to form a hydrophilic binding site; (c) removing the remaining etch mask; and (d) processing the remaining region of the hydrophobic layer to recover its original hydrophobic properties.

In another aspect, the invention provides a method for manufacturing a biochip, comprising: processing the surface of the hydrophilic binding site of an array plate manufactured using the above method, and applying a solution containing biomolecules to the surface of the hydrophilic binding site.

BRIEF DESCRIPTION OF THE DRAWINGS

The above and other features, aspects and advantages of the present invention will become more apparent to those of ordinary skill in the art by describing in detail exemplary embodiments thereof with reference to the attached drawings in which.

DETAILED DESCRIPTION OF THE INVENTION

Korean Patent Application No. 2002-26730, filed on May 15, 2002, and entitled "Process for producing array plate for biomolecules having hydrophilic and hydrophobic regions," is incorporated herein in its entirety.

The present invention will now be described more fully hereinafter with reference to the accompanying drawings, in which a preferred embodiment of the invention is shown. Embodiments of methods for manufacturing an array plate for biomolecules and a biochip using the array plate according to the present invention are provided below. The invention may, however, be embodied in different forms and should not be construed as limited to the embodiments set forth herein. Rather, these embodiments are provided so that this disclosure will be thorough and complete, and will fully convey the scope of the invention to those skilled in the art. It will also be understood that when a layer is referred to as being "on" another layer or substrate, it can be directly on the other layer or substrate, or intervening layers may also be present.

Figure 3:
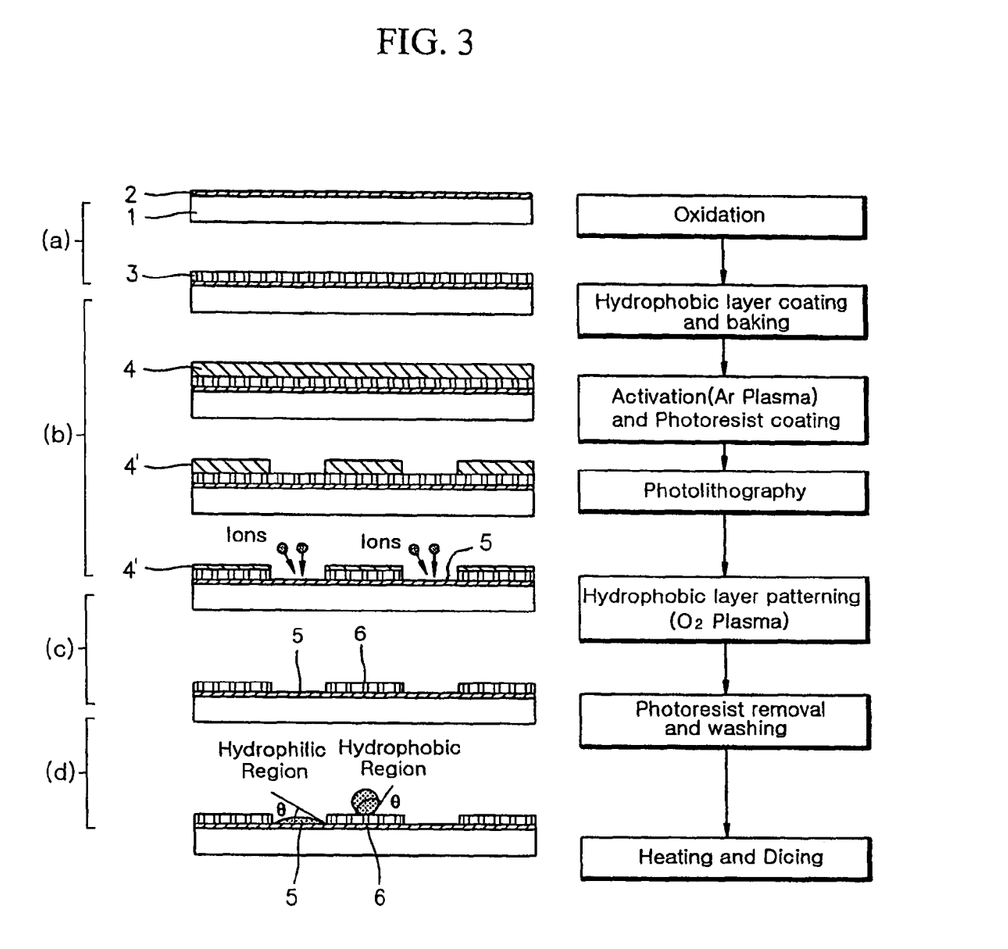
FIG. 3 illustrates the structure of an array plate for biomolecules and a method for manufacturing the same according to an embodiment of the present invention.

Referring to FIG. 3, a method for manufacturing an array plate for biomolecules according to an embodiment of the present invention involves coating a surface of a substrate 1 with a hydrophobic material to form a hydrophobic layer 3 (step (a)). The hydrophobic layer 3 is then etched through an etch mask 4' placed thereon to form a hydrophilic binding site 5 (step (b)). After the etch mask 4' is removed (step (c)), the remaining region of the hydrophobic layer, i.e., hydrophobic region 6, is processed to recover its original hydrophobic properties (step (d)). Details of each of these steps will be described below.

In step (a), suitable materials for the substrate include, but are not limited to, glass, quartz, silicon, ceramic, plastic, metal, etc. The hydrophobic material may be any material capable of being formed as a film and having hydrophobic properties. Examples of such hydrophobic materials include, for example, fluorocarbon polymers such as polytetrafluoroethylene, fluorinated polyimide, fluorinated polyacrylate, fluorinated polyether, and the like; polyhydrocarbons such as polystyrene, polyethylene and derivatives thereof, polynorbornene and derivatives thereof, and the like; polyesters such as polyethylene terephthalate (PET), and the like; diamond-like carbon; and the like.

In step (a), the hydrophobic layer (3) may be formed using a coating of hydrophobic material through known processes in the related fields, for example, spin coating, plasma enhanced chemical vapor deposition (PECVD), a method of forming a self-assembled monolayer, evaporation, dipping, and the like. The resulting hydrophobic layer 3 may have, but is not limited to, a thickness of from tens of angstroms to a few micrometers. After completion of the formation of the hydrophobic layer 3, the substrate 1 having the layer of hydrophobic layer 3 is subject to soft baking and hard baking at a temperature between about 100-200° C. for about 1-30 minutes to remove a solvent and for outgassing from the hydrophobic layer. The hydrophobic layer is then subject to activation using argon (Ar) or oxygen ($O_2$) gas in a plasma state for subsequent spin coating with a photoresist or another metallic mask material.

A method for manufacturing an array plate for biomolecules according to the present invention may further include, before step (a) of coating the hydrophobic layer, forming a hydrophilic layer 2 on the surface of the substrate 1, as shown in FIG. 3. The hydrophilic layer 2 may be a native oxide layer. Such a hydrophilic layer, including native oxide layers, is formed of; for example, $SiO_2$, $Al_2O_3$, SiON, aluminum nitride, polymethylmethacrylate (PMMA), polymethylacrylate (PMA), polyvinyl alcohol (PVA), polyhydroxystyrene, polyacetonitrile, polyacrylic acid, or polytetrahydrofuran. The hydrophilic layer 2 may be formed using, for example, spin coating, thermal wet oxidation, thermal dry oxidation, plasma enhanced chemical vapor deposition (PECVD), or other suitable methods.

According to the present invention, in step (b), the hydrophobic layer 3 formed in step (a) is coated with a mask material and subject to exposure, development, and patterning to form an etch mask 4'. The etch mask 4' is then used to expose a region of the hydrophobic layer 3 that will become a hydrophilic region. It is this hydrophilic region that acts as a binding site 5 in a resulting array plate. The etch mask may be formed of, for example, photosensitive polymers containing negative or positive photoresist, metal hard mask materials, $SiO_2$, polysilicon, or silicon nitride. Such a hydrophilic region may be formed in a recessed or an elevated configuration with respect to the hydrophobic region depending on the nature and characteristics of a desired binding site.

In step (b), the region of the hydrophobic layer exposed through the etch mask 4' is etched to form the hydrophilic binding site 5. Etching may be performed using dry etching or wet etching. For wet etching, the substrate 1 with the hydrophobic layer 3 may be immersed in an etchant to dissolve and wash away the exposed region of the hydrophobic layer 3 and expose the hydrophilic binding site 5. Suitable examples of such an etchant include, but are not limited to, $H_2SO_4$, $H_3PO_4$, $H_2O_2$, HF, HCl, and $NH_4OH$. Dry etching may be performed using plasma gas through reactive ion etching (RIE), ashing, and the like until the hydrophilic binding site 5 is exposed. Suitable examples of such etching gas include, but are not limited to, $O_2$, Ar, $SF_6$, $CF_4$, $BCl_3$, $Cl_2$, and $SiCl_2$, and $O_2$ or Ar is preferred.

In step (c), the etch mask 4' remaining after step (b) of etching is removed to expose a hydrophobic region 6. During the dry etching such as RIE or the wet etching using chemicals, the photoresist etch mask 4' may not be completely removed. For example, when the photoresist etch mask 4' is too thick or has a low etch rate, some amount of the etch mask may remain after etching is conducted to expose the hydrophobic layer 3. Accordingly, any remaining photoresist etch mask 4' may be removed using a photoresist stripper, such as $H_2SO_4$, $H_2O_2$, acetone, and the like. Alternatively, any remaining photoresist etch mask 4' may be removed by extending the duration or period of etching to the hydrophobic layer 3. When a metallic hard mask is used, an etching technique appropriate for removing the hard mask may be applied.

In step (d) of the present invention, the initial hydrophobic properties of the hydrophobic layer 3 may be recovered. In general, hydrophobic layers formed of, for example, fluorocarbon polymers, polyhydrocarbons, etc., lose their hydrophobic properties at least to some extent while undergoing Ar activation, etching, and etch mask removal processes. For example, the water contact angle of such a hydrophobic layer may be reduced to about 50 degrees. In step (d), the initial hydrophobic properties of the hydrophobic layer 3 that have been lost to some extent are recovered, for example, through thermal treatment. This thermal treatment may be performed at a temperature equal to or above the temperature of baking performed after the coating of the hydrophobic layer 3, for example, between about 100-200° C. for about 1-30 minutes. As a result, the hydrophobic properties of the hydrophobic layer 3 are recovered, for example, with a water contact angle of 105 degrees. It is preferable that the surface of the final hydrophobic region 6 has a water contact angle of 105 degrees or more and a surface energy of about 20 dynes/cm or less. In addition, it is preferable that the surface of the final hydrophilic region, i.e. hydrophilic binding site 5, have a water contact angle of less than about 105 degrees.

A method for manufacturing a biochip according to the present invention comprises: manufacturing an array plate using the above-described method according to the present invention; processing the surface of a hydrophilic binding site of the array plate; and applying a solution containing biological molecules to the surface of the hydrophilic binding site.

The surface of the hydrophilic binding site is processed using a compound capable of increasing the affinity of biomolecules to the hydrophilic binding site. For example, the surface of the hydrophilic binding site may be processed using aminopropyltriethoxysilane to attach an amine group on the surface of the hydrophilic binding site.

Any kind of biomolecules, including nucleic acids, proteins, a substrate of an enzyme, cofactor, ligands, and polysaccharides, etc., may be used for a solution to be applied to the hydrophilic binding site. Such biomolecules may be used alone or in conjugation with another compound and may be used after being dissolved in an appropriate solvent.

A gel matrix-DNA conjugate solution is preferred as a solution for the hydrophilic binding site. The gel matrix-DNA conjugate can be prepared by, for example, covalently bonding oligonucleotides to a gel matrix obtained through the coupling reaction between a polyethylene glycol (PEG) derivative having epoxy groups and a cross-linking agent such as polyethylene glycol diamine having a molecular weight of approximately 10,000 or less. Preferably, the gel matrix used herein is a three dimensional (3D) gel matrix prepared by cross-linking a PEG derivative having polyethylene glycol branches in 2 or more directions with a cross-linking agent.

Figure 4:
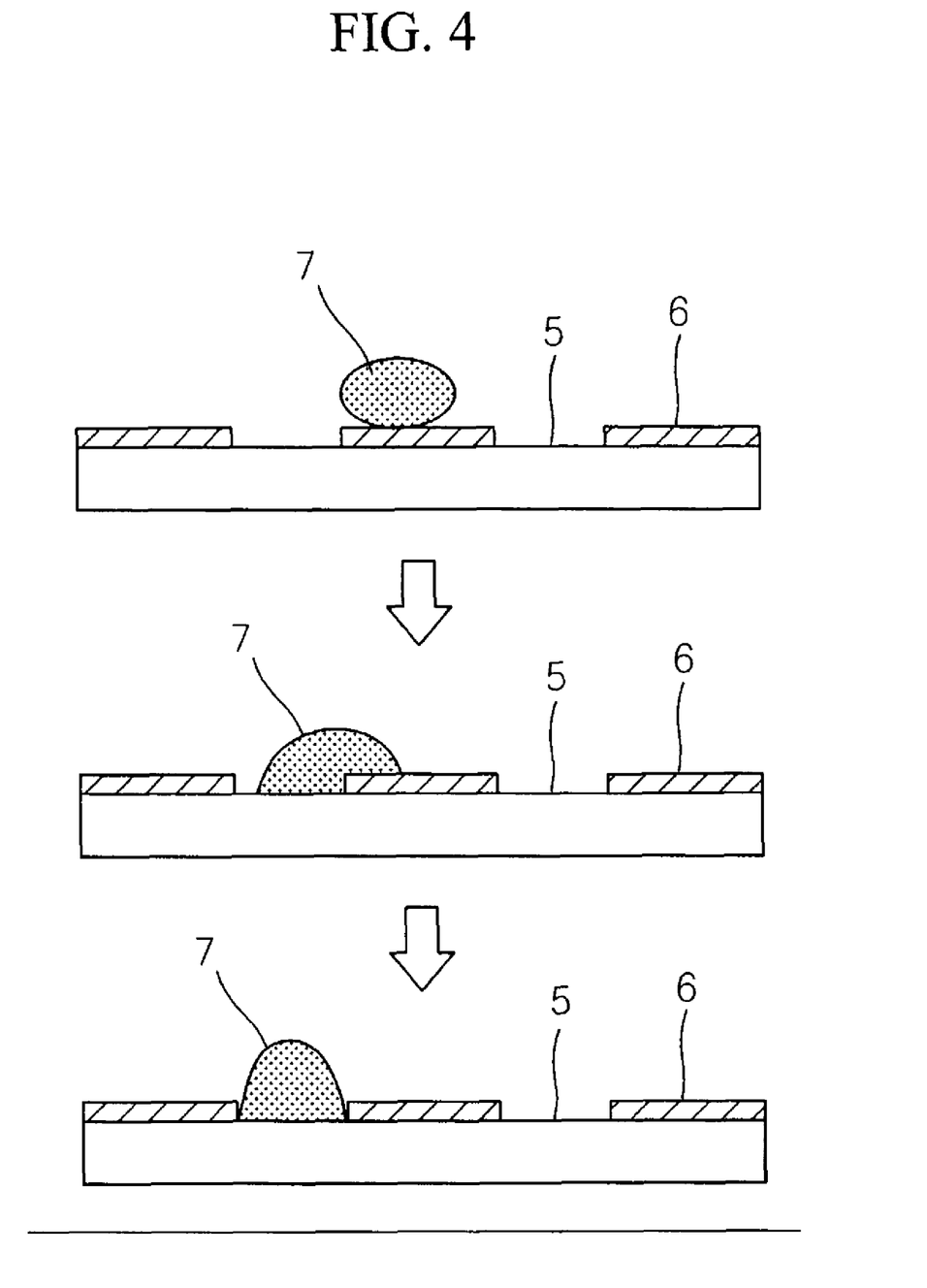
FIG. 4 illustrates the progressive migration of a droplet of biomolecular solution spotted on a hydrophobic region of an array plate to a hydrophilic region due to surface tension.

The PEG derivative includes a PEG derivative which may be formed by reacting a pentaerythritol ethoxylate with epichlorohydrin, as shown in Example 3. A solution containing biomolecules may be applied to the hydrophilic binding site in microdroplets through jetting or spotting using, for example, a piezoelectric pump. Alternatively, a solution containing biomolecules may be applied to the hydrophilic binding site of an array plate by dipping the array plate into the solution. The biomolecules in the solution applied to the hydrophilic binding site may be covalently or non-covalently bound to the hydrophilic binding site of the array plate. Referring to FIG. 4, in a case where the biomolecules 7 are hydrophilic, even though the biomolecules 7 may be spotted on a hydrophobic region 6, the hydrophilic biomolecules migrate to a hydrophilic binding site 5 due to surface tension.

In the manufacture of a biochip according to the present invention, a solution containing biomolecules may be applied to a substrate with a plurality of arrays or to individual arrays after dicing. In dicing, the top surface of a substrate with a plurality of arrays may be covered with a polymer film or a UV tape to protect the hydrophilic binding site from dust contamination during dicing and then uncovered.

A method for manufacturing a biochip according to the present invention may further include, before the application of a solution containing biomolecules to a hydrophilic binding site, coating the surface of the array plate opposite to the hydrophilic and hydrophobic regions with a magnetic material in order to accurately apply the solution containing biomolecules to a desired hydrophilic binding site. Alternatively, this step of coating a magnetic material may be performed after step (a) of forming the hydrophobic layer 3 on the substrate 1 in the manufacture of an array plate according to the present invention. Such a magnetic material may be coated on a substrate with a plurality of arrays or on individual arrays after dicing, before the application of a biomolecule-containing solution as described above. Providing a coating of such magnetic material provides an alignment key for biomolecules to be accurately immobilized on desired binding sites.

Although the binding site of biomolecules in an array plate according to the present invention is described above as being hydrophilic, in an alternative arrangement, an array plate having a hydrophobic binding site and a hydrophilic matrix may be manufactured using the above-described processes in accordance with the present invention. Examples of hydrophobic biomolecules include cell membrane proteins, lipoproteins, etc.

Preferred embodiments of the present invention will now be further described in greater detail by way of the following examples. These examples are provided for illustrative purposes and are not intended to limit the scope of the invention.

Example 1

Manufacture of Array Plates for Biomolecules

A. Hydrophobic Layer Formation Using Fluorocarbon Polymer

On a substrate (0.5 mm thick wafer) having a $SiO_2$ layer (0.05 µm thick layer), a hydrophobic layer was formed by spin coating a hydrophobic material, CYTOP™ (amorphous fluorocarbon, Asahi Glass, Inc., Japan) thereon. Spin coating was performed at 500 rpm for 10 seconds, suspended for 20 seconds, and then at 2000 rpm for 20 seconds. The substrate with the spin coated hydrophobic layer was soft baked at 100° C. for 1 minute and hard baked at 120° C. for 10 minutes. The resulting hydrophobic layer formed of the fluorocarbon polymer had a thickness of about 0.2-0.3 µm.

Next, the surface of the hydrophobic, fluorocarbon polymer layer was activated using Ar in preparation for subsequent spin coating of a layer of photoresist thereon. This activation process was performed for 30 seconds at an Ar flow rate of 100 sccm, a pressure of 0.24 torr, and an RF power of 100 W. Static water contact angle, surface energy, and refractive index were measured for the hydrophobic layer before and after the activation process to determine its hydrophobic properties. The results are shown in Table 1 below.

B. Photoresist Coating and Patterning

The activated surface of the fluorocarbon polymer layer was spin coated with a layer of photoresist, AZ1512™ (Clariant, U.S.A.), followed by soft baking at 100° C. for 1 minute. Spin coating was performed at 500 rpm for 10 seconds, suspended for 20 seconds, and then at 2000 rpm for 20 seconds. The resulting photoresist layer had a thickness of about 1.2 µm. The photoresist layer was patterned into an etch mask through exposure to a light source of 12 mW for 5 seconds and then developed in a solution (containing a developer and water in a 6:1 volume ratio) for 60 seconds. Subsequently, hard baking was performed at 120° C. for 2 minutes.

C. Etching of Fluorocarbon Polymer Layer

The hydrophobic layer of fluorocarbon polymer was etched through the etch mask using reactive ion etching (RIE) at an $O_2$ flow rate of 100 sccm, a pressure of 0.2 torr, and a power of 200 W for 30 seconds to expose a hydrophilic region.

D. Photoresist Removal

The photoresist etch mask used was stripped from the fluorocarbon polymer layer in a solution mixture of $H_2SO_4$ and $H_2O_2$ (in a volume ratio of 4:1) acting as an etchant at 120° C. for 1 minute to expose a hydrophobic region.

E. Recovery of Hydrophobic Properties

After the photoresist removal, the exposed hydrophobic region was thermally treated to recover its original hydrophobic properties. Thermal treatment was performed at 150° C. for 5 minutes and cooled slowly. Static water contact angle, surface energy, and refractive index were measured for the hydrophobic region to determine its hydrophobic properties.

TABLE 1

Surface Characteristics Changes of the Fluorocarbon Polymer Layer After Treatment

| Type of treatment | Surface characteristics | | |
|---|---|---|---|
| | Static water contact angle (degrees) | Surface energy (dynes/cm) | Refractive index |
| Before activation | 110 | 16.7 | 1.35 |
| After activation | 50.1 | 50.1 | 1.37 |
| After thermal treatment | 105 | 20.2 | 1.35 |

As shown in Table 1, after the activation process using Ar, the hydrophobic fluorocarbon polymer layer lost its hydrophobic properties to some extent. Through thermal treatment, however, the hydrophobic properties of the hydrophobic layer were recovered nearly to the original level before the activation.

According to the present invention, an array plate for biomolecules may be manufactured using known coating techniques used in the manufacture of semiconductor devices. Control over the uniformity of the thickness of the hydrophobic layer is therefore easily controlled. As is apparent from the above example, an array plate for biomolecules according to the present invention may be manufactured using semiconductor manufacturing processes with high yield and high accuracy.

Example 2

Manufacture of Array Plates for Biomolecules

An array plate for biomolecules was manufactured in a similar manner as in Example 1, except that the fluorocarbon polymer was coated using PECVD, instead of spin coating used in Step 1 of Example 1. PECVD was performed at a flow rate of 6 sccm for Ar, a flow rate of 4 sccm for $C_4F_8$, a pressure of 0.6 torr, and a power of 30 W for 6 minutes. During the PECVD, the temperature of the substrate was maintained at 75° C. The resulting hydrophobic fluorocarbon polymer had a thickness of about 0.2-0.3 μm.

As a result, it was confirmed that the thermal treatment affects the recovery of the original hydrophobic properties in a hydrophobic region of the array plate. Since the array plate for biomolecules was manufactured using known coating techniques used in the manufacture of semiconductor devices, it was easy to control the thickness of the hydrophobic layer to be uniform. As is apparent from this example, an array plate for biomolecules according to the present invention can be manufactured through semiconductor manufacturing processes with high yield and high accuracy.

Example 3

Manufacture of DNA Chips

DNA chips were manufactured by attaching DNA molecules (SEQ ID No. 1) on the array plates manufactured in Examples 1 and 2 having hydrophilic and hydrophobic regions on substrates. The DNA molecules were attached to the array plates through a gel matrix-DNA molecule.

A. Synthesis of a PEG Derivative Having an Epoxy Group.

7.5 mL of epichlorohydrin and 0.32 g of tetrabutylammonium bromide were added to 2 mL of NaOH solution (50% by weight) and stirred, and 1 g of pentaerythritol ethoxylate was slowly added to the mixture and stirred at room temperature for 18 hours. The completion of the reaction was identified by thin layer chromatography. When the reaction was not completed, the mixture was further stirred for 1 hour at 60° C. Next, the reaction product was diluted with an addition of 30 mL of water and extracted three times with 40 mL of methylene chloride. An organic solvent layer was washed three times with 40 mL of saturated $NaHCO_3$, and anhydrous $MgSO_4$ was added, and the solvent was removed at a low pressure. Next, the resultant product was dried in a vacuum for 2 days to remove the epichlorohydrin residue. The resultant PEG derivative having an epoxy group was identified by H-NMR and titration of the epoxy group using 0.1 N HBr/glacial acetic acid.

B. Synthesis of Diamine Cross-Linking Agent 5 g (9.2 mmol) of penta(ethylene glycol)di-tosylate was dissolved in 40 mL of DMF, and 4.2 g of (64.1 mmol) $NaN_3$ and 0.5 mL of pyridine were sequentially added to the solution and stirred at 140° C. for 18 hours. After removing the solvent at a low pressure, the resultant product was stirred with an addition of 200 mL of water and extracted with 100 mL of methylene chloride. An organic solvent layer was washed three times with 100 mL of brine, and anhydrous $MgSO_4$ was added, and the solvent was removed at a low pressure. Next, the resultant product was subjected to flash column chromatography (EA:nHex=1:2) to isolate a diazide intermediate product. The intermediate product was dissolved in 30 mL of methanol, and 10% Pd—C (0.1 equivalent) was added, followed by a reduction reaction for 18 hours using hydrogen gas. A catalyst was removed using a Celite pad, and the pad was washed with ethanol. The filtrate and the ethanol used to wash the pad were mixed, and the solvent was removed at a low pressure to obtain a diamine cross-linking agent.

C. Preparation of a Gel Matrix-DNA Solution 100 mg of the PEG derivative having an epoxy group as prepared in 1 was stirred with an addition of 4 mL water. 5.8 mg of the diamine cross-linking agent as synthesized in 2 was added to the mixture and stirred at room temperature for 18 hours and stored in a liquid state at 4° C.

Next, to the resultant gel matrix solution, oligonucleotides (SEQ ID NO:1) were added, stirred at 37° C., and left for 14 hours to obtain a spotting solution of a gel matrix-DNA conjugate.

D. Manufacture of Biochip by Spotting a Gel Matrix-DNA Conjugate Solution

Initially, the hydrophilic binding site of each of the array plates was surface treated with aminopropylethoxysilane to form amine groups on the surface. Next, a gel matrix-DNA conjugate solution was spotted onto the aminosilylated binding site, and the array plate was incubated in a humid chamber at 37° C. for 4 hours. To prevent the target nucleic acid from adhering to an unnecessary portion on the glass surface, further reaction is performed such that amino groups at non-spotting positions on the substrate were negatively charged, which is an essential step for controlling background noise, and the resultant biochip was stored in a dryer.

As a result, 90 of 96 DNA chips manufactured in this example were determined as "good" chips and 6 determined as "bad" chips. The 6 bad chips were caused by the unexpected defects in or clogging of nozzles during the spotting of the matrix-DNA conjugate solution and not directly related with the manufacturing technique according to the present invention. DNA chips were assessed as "good" chips when the matrix-DNA conjugate solution was spotted onto all of the hydrophilic binding sites of a chip. The manufacturing yield and accuracy were very high.

According to the present invention, an array plate for biomolecules having hydrophilic and hydrophobic regions can be efficiently manufactured using semiconductor manufacturing processes.

According to the present invention, thermal treatment is performed to recover the hydrophobic properties of a hydrophobic region that degrade during the manufacture of a chip, so that the resulting array plate for biomolecules becomes to have distinct hydrophilic and hydrophobic regions.

According to the present invention, a biochip with biomolecules immobilized thereon can be manufactured using the array plate of high resolution hydrophilic and hydrophobic regions, with high yield and high accuracy.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for manufacturing an array plate for biomolecules, comprising:
    coating a surface of a substrate with a hydrophilic layer;
    coating the hydrophilic layer with a hydrophobic material to form a hydrophobic layer having initial hydrophobic properties, wherein the hydrophobic material is selected from the group consisting of fluorocarbon polymers, polyhydrocarbons, polyesters, and diamond-like carbon;
    baking the substrate;
    forming an etch mask on the hydrophobic layer;
    etching the hydrophobic layer through the etch mask to form an array having at least one hydrophilic site between hydrophobic regions;
    removing the etch mask to uncover at least one hydrophobic region of the array, the uncovered hydrophobic region having reduced hydrophobic properties as compared to the initial hydrophobic properties of the hydrophobic layer; and
    performing a thermal treatment on the at least one uncovered hydrophobic region of the array at a temperature equal to or above a temperature of the baking to form at least one hydrophobic site having improved hydrophobic properties as compared to the reduced hydrophobic properties of the uncovered hydrophobic region, such that the array has distinct hydrophilic and hydrophobic sites, upper surfaces of both the hydrophilic and hydrophobic sites being exposed to an ambient environment,
    wherein at least one of etching the hydrophobic layer and removing the etch mask reduces the hydrophobic properties of portions of the uncovered hydrophobic region.

2. The method as claimed in claim 1, wherein the substrate is formed of glass, quartz, silicon, ceramic, plastic, or metal.

3. The method as claimed in claim 1, wherein:
    the fluorocarbon polymers include amorphous fluorocarbon, polytetrafluoroethylene, fluorinated polyimide, fluorinated polyacrylate, and fluorinated polyether;
    the polyhydrocarbons include polystyrene and polyethylene and derivatives thereof, polynorbornene and derivatives thereof; and
    the polyesters include polyethylene terephthalate.

4. The method as claimed in claim 1, wherein coating the hydrophilic layer includes spin coating, plasma enhanced chemical vapor deposition (PECVD), a method of forming a self-assembled monolayer, evaporation or dipping.

5. The method as claimed in claim 1, wherein the substrate having the hydrophobic layer is soft baked and hard baked at a temperature of about 100° C. to about 200° C. for about 1 minute to about 30 minutes prior to etching the hydrophobic layer.

6. The method as claimed in claim 1, further comprising activating the hydrophobic layer using argon (Ar) or oxygen ($O_2$) gas in a plasma state prior to forming the etch mask, wherein at least one of activating the hydrophobic layer, etching the hydrophobic layer, and removing the etch mask reduces the hydrophobic properties of portions of the uncovered hydrophobic region.

7. The method as claimed in claim 1, wherein a native oxide layer is formed to form the hydrophilic layer on the surface of the substrate.

8. The method as claimed in claim 7, wherein the native oxide layer is formed of $SiO_2$, $Al_2O_3$, SiON, aluminum nitride, polymethylmethacrylate (PMMA), polymethylacrylate (PMA), polyvinyl alcohol (PVA), polyhydroxystyrene, polyacetonitrile, polyacrylic acid, or polytetrahydrofuran.

9. The method as claimed in claim 1, wherein the hydrophilic layer is formed by spin coating, thermal wet oxidation, thermal dry oxidation, or plasma enhanced chemical vapor deposition (PECVD).

10. The method as claimed in claim 1, wherein the etch mask is formed of photosensitive polymers, metal hard mask materials, $SiO_2$, polysilicon, or silicon nitride.

11. The method as claimed in claim 1, wherein the hydrophilic region is formed in a recessed or an elevated configuration with respect to the hydrophobic region.

12. The method as claimed in claim 1, wherein etching the hydrophobic layer includes dry etching or wet etching.

13. The method as claimed in claim 12, wherein the etching includes dry etching, the dry etching being conducted using plasma gas through reactive ion etching (RIE) or ashing.

14. The method as claimed in claim 13, wherein the dry etching is conducted using plasma gas, the plasma gas including $O_2$, Ar, $SF_6$, $CF_4$, $BCl_3$, $Cl_2$, and $SiCl_2$.

15. The method as claimed in claim 1, wherein removing the etch mask includes at least one of use of a photoresist stripper or extension of a length of time that etching the hydrophobic layer is performed.

16. The method as claimed in claim 1, wherein processing the at least one uncovered hydrophobic region of the array includes thermal treatment at a temperature of about 100° C. to about 200° C. for about 1 minute to about 30 minutes.

17. The method as claimed in claim 1, wherein processing the at least one uncovered hydrophobic region is conducted until a surface of the hydrophobic region has a water contact angle greater than or equal to 105 degrees and a surface energy of the surface of the hydrophobic region is about 20 dynes/cm or less.

18. The method as claimed in claim 3, wherein the amorphous fluorocarbon is CYTOPT™.

19. The method as claimed in claim 1, wherein a thickness of the hydrophobic layer is less than about 0.5 μm.

20. The method as claimed in claim 1, wherein etching the hydrophobic layer through the etch mask exposes at least a portion of the hydrophilic layer, to form an array having at least one hydrophilic site between hydrophobic regions.

21. A method for manufacturing a biochip, comprising:
    forming an array plate according to a method, including,
        coating a surface of a substrate with a hydrophilic layer;
        coating the hydrophilic layer with a hydrophobic material to form a hydrophobic layer having initial hydrophobic properties, wherein the hydrophobic material is selected from the group consisting of fluorocarbon polymers, polyhydrocarbons, polyesters, and diamond-like carbon;

baking the substrate;

forming an etch mask on the hydrophobic layer;

etching the hydrophobic layer through the etch mask to form an array having at least one hydrophilic binding site between hydrophobic regions, the hydrophilic binding site having a surface;

removing the etch mask to uncover at least one hydrophobic region of the array, the uncovered hydrophobic region having reduced hydrophobic properties as compared to the initial hydrophobic properties of the hydrophobic layer; and performing a thermal treatment on the at least one uncovered hydrophobic region of the array at a temperature equal to or above the temperature of the baking to form at least one hydrophobic site having improved hydrophobic properties as compared to the reduced hydrophobic properties of the uncovered hydrophobic region, such that the array has distinct hydrophilic and hydrophobic sites, upper surfaces of both the hydrophilic and hydrophobic sites being exposed to an ambient environment;

wherein at least one of etching the hydrophobic layer and removing the etch mask reduces the hydrophobic properties of portions of the hydrophobic layer;

processing the surface of the at least one hydrophilic binding site of the array plate to increase hydrophilicity thereof; and applying a solution containing biomolecules to the array plate.

22. The method for manufacturing a biochip as claimed in claim 21, wherein the surface of the hydrophilic binding site is processed using aminopropyltriethoxysilane to attach an amine group on the surface of the hydrophilic binding site.

23. The method for manufacturing a biochip as claimed in claim 21, wherein the biomolecules are nucleic acids, proteins, substrates of an enzyme, cofactors, ligands, polysaccharides, and mixtures thereof.

24. The method for manufacturing a biochip as claimed in claim 21, wherein the solution containing biomolecules is a gel matrix-DNA conjugate solution.

25. The method for manufacturing a biochip as claimed in claim 24, wherein the gel matrix-DNA conjugate is prepared by covalently bonding DNA to a gel matrix obtained through the coupling reaction between a polyethylene glycol (PEG) derivative having epoxy groups and a cross-linking agent.

26. The method for manufacturing a biochip as claimed in claim 25, wherein the gel matrix is a three dimensional (3D) gel matrix prepared by cross-linking a PEG derivative having polyethylene glycol branches in 2 or more directions with a cross-linking agent.

27. The method for manufacturing a biochip as claimed in claim 25, wherein the cross-linking agent is a polyethylene glycol diamine having a molecular weight of approximately 10,000 or less.

28. The method for manufacturing a biochip as claimed in claim 25, wherein the PEG derivative includes a reaction product of pentaerythritol ethoxylate with epichlorohydrin.

29. The method for manufacturing a biochip as claimed in claim 21, wherein the solution containing biomolecules is applied to a substrate having a plurality of arrays or to individual arrays, the individual arrays being formed by dicing the substrate having a plurality of arrays.

30. The method for manufacturing a biochip as claimed in claim 29, wherein in dicing, the top surface of a substrate with a plurality of arrays is covered with a polymer film or a UV tape to protect the hydrophilic binding site.

31. The method for manufacturing a biochip as claimed in claim 21, further comprising coating the surface of the array plate with a magnetic material after coating the hydrophilic layer with the hydrophobic material.

32. The method for manufacturing a biochip as claimed in claim 21, wherein applying a solution containing biomolecules to the array plate includes applying the solution solely to the at least one hydrophilic binding site.

33. The method for manufacturing a biochip as claimed in claim 21, wherein applying a solution containing biomolecules to the array plate includes applying the solution solely to the hydrophobic binding sites.

34. The method as claimed in claim 21, wherein etching the hydrophobic layer through the etch mask exposes at least a portion of the hydrophilic layer, to form an array having at least one hydrophilic site between hydrophobic regions.

35. The method for manufacturing a biochip as claimed in claim 32, wherein the solution containing biomolecules is applied to the hydrophilic binding site by jetting or spotting or by dipping the array plate into the solution.

36. The method for manufacturing a biochip as claimed in claim 32, wherein the biomolecules in the solution form covalent or non-covalent bonds through chemical reactions with the hydrophilic binding site of the array plate.

37. The method for manufacturing a biochip as claimed in claim 32, further comprising coating the array plate with a magnetic material in order to accurately apply the solution containing biomolecules to a desired hydrophilic binding site prior to coating the hydrophilic layer with the hydrophobic material or prior to applying the solution containing biomolecules to the array plate.

38. The method for manufacturing a biochip as claimed in claim 33, wherein the biomolecules include cell membrane, proteins, and lipoproteins.

39. The method as claimed in claim 12, wherein the etching includes wet etching, the wet etching including the substrate with the hydrophobic layer being immersed in an etchant to dissolve and wash away an exposed region of the hydrophobic layer and expose a hydrophilic binding site.

40. The method as claimed in claim 39, wherein the etchant is $H_2SO_4$, $H_3PO_4$, $H_2O_2$, HF, HCl, or $NH_4OH$.

* * * * *